United States Patent
Hubbell et al.

(10) Patent No.: US 6,943,211 B1
(45) Date of Patent: Sep. 13, 2005

(54) POLYMER COMPOUNDS

(75) Inventors: Jeffrey A. Hubbell, Zumilon (CH); Petra van de Wetering, Zürich (CH); Didier Cowling, Langnau an Albis (CH)

(73) Assignee: Life Medical Sciences, Inc., Little Silver, NJ (US)

( * ) Notice: Subject to any disclaimer, the term of this patent is extended or adjusted under 35 U.S.C. 154(b) by 376 days.

(21) Appl. No.: 09/644,121

(22) Filed: Aug. 23, 2000

Related U.S. Application Data

(63) Continuation-in-part of application No. 09/256,484, filed on Feb. 23, 1999.

(51) Int. Cl.$^7$ ................................................ C08F 8/00
(52) U.S. Cl. ................. 524/556; 525/326.7; 525/329.9; 525/330.5
(58) Field of Search ............................. 525/326.7, 329.9, 525/330.5; 524/556

(56) References Cited

U.S. PATENT DOCUMENTS

| | | | |
|---|---|---|---|
| 5,080,893 A | | 1/1992 | Goldberg et al. |
| 5,140,016 A | | 8/1992 | Goldberg et al. |
| 5,154,706 A | | 10/1992 | Cartmell et al. |
| 5,160,328 A | | 11/1992 | Cartmell et al. |
| 5,204,110 A | | 4/1993 | Cartmell et al. |
| 5,302,312 A | * | 4/1994 | Kawai et al. ............ 510/113 |
| 5,306,504 A | | 4/1994 | Lorenz |
| 5,350,573 A | | 9/1994 | Goldberg et al. |
| 5,423,736 A | | 6/1995 | Cartmell et al. |
| 5,665,477 A | | 9/1997 | Meathrel et al. |
| 5,705,177 A | | 1/1998 | Roufa et al. |
| 5,705,178 A | | 1/1998 | Roufa et al. |
| 5,885,566 A | | 3/1999 | Goldberg |
| 5,906,997 A | | 5/1999 | Schwartz et al. |
| 5,920,158 A | | 7/1999 | Miller et al. |
| 5,939,208 A | | 8/1999 | Stoy |
| 5,994,325 A | | 11/1999 | Roufa et al. |
| 5,994,475 A | * | 11/1999 | Roth et al. ............ 525/326.7 |
| 6,010,692 A | | 1/2000 | Goldberg et al. |
| 6,017,301 A | | 1/2000 | Schwartz et al. |
| 6,034,140 A | | 3/2000 | Schwartz et al. |
| 6,083,930 A | | 7/2000 | Roufa et al. |
| 6,127,348 A | | 10/2000 | Roufa et al. |
| 6,133,325 A | | 10/2000 | Schwartz et al. |
| 6,417,173 B1 | | 7/2002 | Roufa et al. |
| 2002/0010150 A1 | | 1/2002 | Cortese et al. |

FOREIGN PATENT DOCUMENTS

| | | |
|---|---|---|
| EP | 0068509 B1 | 8/1985 |
| EP | 0426422 A2 | 10/1990 |
| EP | 0604101 A1 | 12/1993 |
| EP | 0952171 A2 | 10/1999 |
| GB | 2215335 A * | 9/1989 |
| WO | WO 92/06748 | 4/1992 |
| WO | WO 95/15352 | 6/1995 |
| WO | WO 97/05185 | 2/1997 |
| WO | WO 99/44557 | 9/1999 |
| WO | WO 99/47129 | 9/1999 |
| WO | WO 00/44808 | 8/2000 |
| WO | WO01/82863 A2 | 11/2001 |
| WO | WO01/82937 A1 | 11/2001 |

OTHER PUBLICATIONS

Fate of Water–Soluble Polymers Administered via Different Routes, Tetsuji et al.; J of Pharm. Sci vol. 84, No. 3, Mar. 1995, p. 349–354.

* cited by examiner

*Primary Examiner*—Bernard Lipman
(74) *Attorney, Agent, or Firm*—Coleman Sudol Sapone, P.C.

(57) ABSTRACT

Provided is a composition comprising a pre-formed, hydrolytically susceptible non-addition polyanionic polymer comprising polymer strands formed from at least one ethylenically unsaturated monomer and linking the polymer strands by at least one linking moiety comprising a hydrolytically susceptible bond, wherein at least one of which monomers has: i) one or more functional groups that can be titrated with base to form negatively charged functional groups; or ii) one or more precursor groups that are precursors of the functional groups that can be titrated with base; which precursor groups are converted to the functional groups.

6 Claims, No Drawings

POLYMER COMPOUNDS

This application is a continuation-in-part of U.S. Ser. No. 09/256,484, filed Feb. 23, 1998, pending.

The invention provides compositions comprising a polyanionic polymer, preferably a hydrogel polyanionic polymer, some of which compositions can form a microgel. Polymeric polymers, including polymeric hydrogels, have been developed for medical treatments. Some polymers of the invention, when hydrated, can form either an elastic solid, a viscoelastic solid (like a typical solid gel, for example, a gel like gelatin), a viscoelastic liquid (like a typical gel that can be induced to flow, for example, a gel like petroleum jelly), a viscoelastic liquid that is formed of gel microparticles (such as a Carbopol™ gel) or even a viscous liquid.

Hydrogels are polymeric materials that are highly swollen with water. For many applications, hydrogels are especially useful. Hydrogels are of interest for myriad biomedical applications. These include, but are not limited to, barrier applications (adhesion preventives, sealants), drug delivery devices, tissue engineering and wound healing scaffolds, and materials for cell encapsulation and transplantation:

Hydrogels as glues or sealants are desirable to seal leaks in tissues that isolate (gas or liquid phase) fluid-containing cavities. Some examples are blood vessels, the skin, the lung, the blood-brain barrier, and the intestine.

Carbomers are one type of cross-linked hydrogels formed primarily of polyacrylic acid (PAA) based polymers. These gels are formed by free radical polymerization of acrylic acid (AA) in the presence of a multifunctional co-monomer, which thereby serves as a crosslinking agent, for example, (1). These gels can be polymerized under conditions such that microgels form, i.e. small (1–200 µm in the swollen state) cross-linked beads, each bead of which is a cross-linked viscoelastic solid, but the conglomeration of many of which acts like a viscoelastic fluid by virtue of flow of one viscoelastic solid particle over another. The cross-link density and thereby the physical properties of the resulting carbomer microgel can be controlled relatively well by manipulation of the cross-link density, which in turn is controlled by the molar ratio of crosslinking agent to acrylic acid monomer. The physical properties are controlled primarily by the interpretation of chains from the surface of one microgel particle into neighbouring microgel particles and by the elasticity of the microgel particles.

Carbomers have been designed to be hydrolytically stable. The PAA chain is very stable to hydrolysis, and the crosslinking agent typically utilized is also stable to hydrolysis. The biomedical applications envisioned in this invention benefit from hydrolytic sensitivity, namely degradation into smaller components suitable for elimination from the body. Preferably, the polymer particles degrade into soluble polymer chains that can be eliminated through the kidney. In traditional uses of carbomers, stability is desired and hydrolytic instability is not desired. In the case of the invention, hydrolytically susceptible (i.e., unstable) carbomers are desired.

Linear and branched, but not cross-linked, PAA-based polymers can also be useful in a variety of applications. To achieve viscoelastic character, as would be obtained with cross-linked Carbomers, high molecular weight polymers are utilized. Analogously to the cross-linked Carbomers, polymers with hydrolytically stable high molecular weight are typically utilized. By contrast, in this invention polymers with a hydrolytically susceptible (i.e., unstable) high molecular weight are sought.

Natural proteins and modified or recombinant proteins are widely tested for biomedical applications. Collagen and denatured coltagens (gelatines) are widely used or tested for applications requiring a three-dimensional material. These materials are reversible by melt above their gelation temperatures unless they are chemically crosslinked, with glutaraldehyde for example. A fibrin gel or clot is a biochemically crosslinked version of the self-assembled fibrin monomer gel, both arising naturally in the coagulation cascade.

Carbohydrate-based gels are also studied for biomedical applications. Forms of cellulose, hyaluronic acid, and alginate have received much attention. Some carbohydrates, such as hyaluronic acid, can form gel-like materials simply by forming highly viscous solutions in aqueous media. The carbohydrates can also be crosslinked chemically, with glutaraldehyde for example, to form gels.

SUMMARY OF THE INVENTION

The invention relates to compositions comprising a polyanionic polymer. In some embodiments, the polyanionic polymer can form a microgel, typically meaning that the polymer is appropriately crosslinked. In some embodiments, the polymers are carbomers. In some embodiments, the polyanionic polymers are pre-formed hydrolytically susceptible non-addition polymers as defined below.

In some embodiments, the invention provides compositions which can include compounds that can form a microgel comprising a crosslinked polyanionic polymer, preferably a pre-formed, hydrolytically susceptible non-addition polyanionic polymer comprising polymer strands formed from at least one ethylenically unsaturated monomer, wherein the polymer strands are linked by at least one linking moiety comprising a hydrolytically susceptible bond, wherein at least one of which monomers has:

i) one or more functional groups that can be titrated with base to form negatively charged functional groups, or ii) one or more precursor groups that are precursors of the functional groups that can be titrated with base; which precursor groups are converted to the functional groups;

wherein, preferably, at least one of the ethylenically unsaturated monomers is according to the formula:

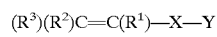  I wherein:

Y is $-C(O)OR^4$; $-O-S(O_2)OR^4$; $-S(O_2)OR^4$; or $-S(O)OR^4$; wherein $R^4$ is hydrogen or a cleavage permitting group, preferably, $C_1$ to $C_6$ normal or branched alkyl, phenyl, or benzyl;

X is a direct bond; a straight or branched alkylene group having two to six carbon atoms, one or more of which can be replaced by O, S, or N heteroatoms, provided that there is no heteroatom in a position α or β to Y; phenylene; a five or six membered heteroarylene having up to three heteroatoms independently selected from O, S, and N, provided that neither Y or $R^3R^2C=C(R^1)$ is bonded to a heteroatom (phenylene, oxazolylene, isoxazolylene, pyridazinylene, pyrimidinylene are examples of preferred arylenes); and $R^1$, $R^2$, and $R^3$ are independently selected from, hydrogen, $C_1$–$C_6$ alkyl (or $C_1$–$C_4$ or $C_1$–$C_3$ alkyl), carboxy, halogen, cyano, isocyanato, $C_1$–$C_6$ hydroxyalkyl (or $C_1$–$C_4$ hydroxyalkyl), alkoxyalkyl having 2 to 12 (or 2 to 6) carbon atoms, $C_1$–$C_6$ haloalkyl (or $C_1$–$C_4$), $C_1$–$C_6$cyanoalkyl (or $C_1$–$C_4$), $C_3$–$C_6$cycloalkyl, $C_1$–$C_6$ carboxyalkyl (or $C_1$–$C_4$ carboxyalkyl), aryl, hydroxyaryl, haloaryl, cyanoaryl, $C_1$–$C_6$ alkoxyaryl (or $C_1$–$C_4$ alkoxyaryl), carboxyaryl, nitroaryl, or a group —X—Y; wherein alkylor alkoxy groups are either linear or branched and up to Q-2 carbon atoms of any $C_3$–$C_6$ cycloalkyl group, wherein Q is the total number of ring carbon atoms in the cycloalkyl group, are independently replaced with O, S, or N heteroatoms; with the proviso that neither doubly-bonded carbon atom is directly bonded to O or S; and wherein aryl is phenyl or a 5 or 6 membered heteroaryl group having up to three heteroatoms selected from the group consisting of O, S, and N. In some embodiments of the invention, $R^1$, $R^2$ and $R^3$ can be independently hydrogen or $C_1$–$C_3$ alkyl and X is a direct bond or $C_1$–$C_3$ alkylene. The cleavage permitting group can include, in some embodiments, one or more $C_1$ to $C_6$ normal or branched alkyl, phenyl or benzyl groups. In the above structure, aryl means phenyl or a 5 or 6membered heteroaryl group having up to Q-2 heteroatoms independently selected from O, S, and N; wherein Q is the total number of atoms in the ring.

In some embodiments, a microgel can be formed of the polyanionic polymer. In some embodiments, the linking moiety is formed by co-polymerization (in a polymer-forming reaction) of an ethylenically unsaturated linking agent, where preferably the mole fraction of ethylenic double bonds in the combination from which the polyanionic polymer is made that is contributed by the ethylenically unsaturated linking agent is 0.02 or less, preferably 0.01 or less. In some embodiments of the invention, the ethylenically unsaturated linking agent is an allylether of sucrose or an allyl ether of pentaerythritol. In some embodiments, the ethylenically unsaturated linking agent can be, for example, an allyl ether of pentaerythritol or pentaerythritol triacrylate. In some embodiments, the unsaturated linking agent is an acrylate of pentaerythritol. In some embodiments, the unsaturated linking agent can be an acrylate-ester-acrylate pentaerythritol. In some embodiments, the polymers of the invention can be used in a microgel wherein the ratio of macroviscosity of the microgel to the microviscosity is 10,000 or less.

In some embodiments, the polyanionic polymer is functionalized to provide one or more pendant functional groups selected from hydroxy, acyl halide, chloroformate, and mercapto, while the linking moiety provides linking and is a reaction product of the pendant groups between polymer segments or between the pendant groups and complementing functional groups of a linking agent In some embodiments, the pendant functional groups can be mercapto groups and the complementing functional groups of the linking agent can be vinylic double bonds. The linking agent can be the diacrylate of an α,ω-diol, such as ethylene glycol or polyethylene glycol, or the diacrylate of a chain extended α,ω-diol, wherein the chain extensions comprise residues of a hydroxy carboxylic acid such as glycolic acid, lactic acid, 3-hydroxypropionic acid, livdroxylated 3-methylbutyric acid, hydroxyvaleric acid and hydroxy proline (hydroxylated $C_2$–$C_5$ carboxylic acids and hydroxy proline) or residues of an amino acid such as glycine, alanine, glutamic acid, and aspartic acid. In some embodiments, the pendant functional groups can be hydroxyl groups, the complementing functional groups can be carboxylic acid chloride or chloroformate groups, and the linking agent can comprise a residue of either an α,ω-diol or a chain extended α,ω-diol. In some embodiments, the functionalized polyanionic polymer comprises acrylic acid monomers and has at least one N-(2-mercapto)ethyl carboxamide group, optionally also having at least one pendant functional group that is a mercapto group.

In some embodiments, the ethylenically unsaturated linking agent comprises multidentate compound comprising two or more two or more ethylenically unsaturated moieties, each such moiety being linked to the multidentate compound through a hydrolytically susceptible bond. The multidentate compound can be an α,ω-diol, such as ethylene glycol, diethylene glycol, or polyethylene glycol. The multidentate compound can be an α,ω-diamine, such as ethylene diamine. In some embodiments, the multidentate compound can be, for example, an amino aliphatic alcohol, an amino aliphatic diol, an amino aliphatic triol, a hydroxyl aliphatic diamine, and a hydroxyl aliphatic triamine an amino aliphatic thiol, an amino aliphatic dithiol, an amino aliphatic trithiol, a mercapto aliphatic diamine, or a mercapto aliphatic triamine. The hydrolytically susceptible bond can be formed from one or more residues of a hydroxy carboxylic acid such as hydroxylated $C_2$–$C_5$ carboxylic acids and hydroxy proline. The hydrolytically susceptible bond can be formed from, in some embodiments, at least one residue of an amino acid.

In some embodiments, a polyanionic polymer has a main chain comprising one or more hydrolytically susceptible bonds selected from the group consisting of ester, carbonate, thiocarbonate, urethane, carbamate and urea bonds. In some embodiments, one or more hydrolytically susceptible bonds can derive from a residue of a hydroxy acid. The main chain of the polyanionic polymer can include a residue of an α,ω-diol, diamine or dithiol.

Some embodiments provide a polyanionic polymer formed by the reaction of the bis-acrylate of ethylene glycol, the bis-acrylamide of ethanediamine, or N2-acryloyloxy) ethyl acrylamide with a bis-mercapto end-capped polyanionic oligomer and made by polymerization of one or more ethylenically unsaturated monomers. Provided is, in one embodiment, polyanionic polymer comprising hydrolytically susceptible bonds comprising: two or more polyanionic polymer segments; linking moieties coupling the polyanionic polymer segments wherein the linking moieties comprise (I) or (II) below or both:

(I) a segment joining joined via amide, ester or thioester bonds incorporating an acyl or acyl analog moiety of the polyanionic polymer, wherein the segment comprises: (a) a $C_1$ to $C_{12}$ alkylene (which alkylenes here and for those recited below in this paragraph can be $C_1$ to $C_{10}$ or $C_1$ to $C_5$) with terminal linkers selected from oxy, thio (—S—) or imino (—NR—, where R is H or $C_1$–$C_6$ alkyl) incorporated into the amide, ester or thioester bonds, provided that at least one of the amide, ester or thioester bonds is other than an ester bond; or (b) an amide, ester or thioester linked polymeric segment of (i) hydroxy or a thiol $C_2$–$C_5$ carboxylic acid or hydroxy proline derivatives and (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) an α,ω-diol or a chain extended α,ω-diol}; or (c) an amide, ester or thioester linked polymeric segment of (i) one or more hydroxy or thiol $C_2$–$C_5$ carboxylic acid or hydroxy proline derivatives, (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) one or more α,ω-diols or chain extended α,ω-diols} and (iii) one or more carbonyldioxy moieties; or (d) an amide, ester or thioester linked polymeric segment of (ii)(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds, (ii)(b) one or more chain extended α,ω-diols and (iii) one or more carbonyldioxy moieties; or (e) an amide, ester or thioester linked polymeric segment of (ii)(b) one or more chain extended α,ω-diols and (iii) one or more carbonyldioxy moieties; or (f) a direct anhydride formed between acid moieties of the polyanionic polymer; or (g) an anhydride bridge formed between acid moieties of the polyanionic polymer with carbonyl bridge; or (I) the residue after a crosslinking reaction of:
  (a) two or more terminal acrylate or methacrylate moieties providing unsaturated bonds available for the crosslinking reaction;
  (b) a segment joining the terminal acrylate or methacrylate moieties via amide, ester or thioester bonds incorporating an acyl bond of the acrylate or methacrylate moieties, wherein the segment comprises:
    (1) a $C_1$ to $C_{12}$ alkylene with terminal linkers selected from oxy, thio (—S—) or imino (—NR—, where R is H or $C_1$–$C_6$ alkyl) incorporated into the amide, ester or thioester bonds, provided that at least one of the amide, ester or thioester bonds is other than an ester bond; or (2) an amide, ester or thioester linked polymeric segment of (i) hydroxy or thiol $C_2$–$C_5$ carboxylic acid or hydroxy proline derivatives and (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) an α,ω-diol or a chain extended α,ω-diol}; or (3) an amide, ester or thioester linked polymeric segment of (i) one or more hydroxy or thiol $C_2$–$C_5$ carboxylic acid or hydroxy proline derivatives, (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) one or more α,ω-diols or chain extended α,ω-diols} and (iii) one or more carbonyldioxy moieties; or (4) an amide, ester or thioester linked polymeric segment of (ii)(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds, (ii)(b) one or more chain extended α,ω-diols and (iii) one or more carbonyldioxy moieties; or (5) an amide, ester or thioester linked polymeric segment of (ii)(b) one or more chain extended α,ω-diols and (iii) one or more carbonyldioxy moieties.

In one embodiment, the invention provides a polyanionic polymer comprising: two or more linearly linked polyanionic polymer segments linked via terminating oxo or thio moieties derived from a hydroxide or thiol moieties; and linker moieties cleavable at internal amide, ester or thioester bonds linking the linkers to form the linear polyanionic polymer segments. The polyanionic polymer can comprise a monomer moiety which consists of atoms selected from carbon, hydrogen, oxygen and sulfur and comprises carbon and hydrogen. The linearly linked polyanionic segments can be crosslinked hydrolytically susceptible linking moieties.

Other objects, features, and advantages of the invention will be apparent to those of ordinary skill in the art from the following detailed description of the invention.

DETAILED DESCRIPTION OF THE INVENTION

For the purposes of this application, the terms listed below shall have the following respective meanings:

AM is an anionic monomer consistent with the monomers described in the Summary.
  Note that consistent with the Summary and the further description below, not all of the monomer contributing to a PAP is itself anionic.
MW is molecular weight.
PAA is a Poly(acrylic acid) based polymer.
PAO is polyalkylene oxide, of which PEG is an example. PAOs are typically have C2 to C4 repeating units, with C3 and C4 repeating units typically blended with C2 (ethyleneoxide) to increase water solubility. The size of the PAO segments is preferably such the molecular weights for 90% or more of the segments is 50 kd or 40 kd or less. In one embodiment, 95%, 98% or more of the segments fall within these size limits. Preferably, the average molecular weight of the segments is from 20 kd to 40 kd, or 25 kd to 35 kd. Preferably, PAO segments have molecular weight averages of at least 500, more preferably at least 1,000.
PAP is a polyanionic polymer in accordance with the polymer described in the Summary.
PEG is polyethylene glycol.
acid number refers to the amount of potassium hydroxide in milligrams needed to neutralize a gram of a dry material. A material is dry if it contains not more that 2% by weight of water, an organic solvent, or organic monomer.
aliphatic includes both aliphatic and cycloaliphatic, unless otherwise indicated.
alkyl means a linear or branched alkyl group having 1–6 carbon atoms and including halogen substitution of one or more of the hydrogens of the alkyl group.
amide, ester or thioester includes, for the present purposes, the amide, ester or thioester moieties incorporated into carbonate or carbamate moieties, or their thio-containinig analogs.
cleavage-permiting group means a moiety containing $OR^4$ in which the $OR^4$ group can be chemically altered, substituted or exchanged so that the residue is —OH or —O.
effective amount: The meaning of "effective amount" will be recognized by clinicians but includes an amount effective to reduce, ameliorate or eliminate one or more symptoms of the disease sought to be treated or the condition sought to be avoided or treated, or to otherwise produce a clinically recognizable change in the pathology of the disease or condition.
hydrogel is a combination with water of a hydrophilic polymer, which may be linear, branched, covalently crosslinked, ionically crosslinked, physically crosslinked, or crosslinked by hydrogen bonding. A hydrogel has 50% or more water by weight. Examples of hydrophilic polymers that form hydrogels are carboxymethylcellulose, carboxypolymethylene, and poly(hydroxyethyl methacrylate).
hydrolytically susceptible: A hydrolytically susceptible polymer is one that contains ester, amide, carbamate or anhydride bonds, or the sulfur or nitrogen-containing analogs (such as ureylene groups, imidoesters, thioesters, and the like) positioned to allow the polymer to hydrolyze over time to smaller component polymers. Such bonds are hydrolytically susceptible bonds.
labile spacer group shall include a chemical functional group which is susceptible to enzymatic or nonenzymatic hydrolysis or oxidation. The labile spacer group can, in some embodiments, have one or more residues of a hydroxy carboxylic acid such as glycolic acid, lactic acid, 3-hydroxypropionic acid, 3-methylbutyric acid, hydroxyvaleric acid, or hydroxy proline. The labile spacer group can include, in some embodiments, at least one residue of an amino acid. Optionally, the hydrolytically susceptible bonds are substituted with labile spacer groups.

linking moiety comprising a hydrolytically susceptible bond refers to a chemical moiety including at least one hydrolytically susceptible bond that links one segment of polymer to another. Such a linking moiety can join two ends of linear polymer, thereby lengthening the polymer, or provide a crosslinker. Linking moieties can be formed with linking agents or by reaction of functional groups on respective segments of polymer.

microgel means a viscoelastic mass of discrete particles, each discrete particle comprising crosslinked polyanionic polymer and each particle having a size in its aqueous swollen state at neutral pH of between 0.1 and 1000 μm. The particles of aqueous swollen polyanionic polymer have 70% or more water and the crosslinking is ionic, covalent, or through hydrogen bonding.

microviscosity is measured, for example, by any method set forth in R. Y. Lochhead et al., "Poly(acrylic acid) Thickeners: The Importance of Gel Microrheology and Evaluation of Hydrophobically Modified Derivatives as Emulsifiers," in *Polymers in Aqueous Media*, pp. 113–147, 1989, which document is incorporated by reference herein in its entirety. One such method measures microdiffusion with bimodal gold sols, for example allowing for microdiffusion to be measured for a microstructure centered around 10 nm and 100 nm.

mono or disaccharide means such a saccharide or disaccharide (such as sucrose), which can be reduced to the nonreducing form or oxidized to contain up to one carboxylic acid.

multidentate compound is a compound having two or more functional groups, for example selected from hydroxy, amino, or mercapto (thiol). Examples of multidentate compounds include ethylene glycol, amino ethanol, polyethylene glycol, glycerol, and pentaerythritol.

neutral functional group means a functional group that is not titrated by acid or base.

non-addition polymer is a polymer wherein the polyanionic polymer segments are not formed by the addition reaction of a strong nucleophile (excluding radicals) with an ethylenic unsaturation in a second molecule. Provided this condition is met, a non-addition polymer, for the purposes of this application, can include any polymers where such polyanionic segments are produced by any means including free-radical polymerization, cationic polymerization, or anionic polymerization, as well as polymers formed by condensation reactions. It should be understood that the linking moieties or linking agents used in, or used to form, the polymers can be formed by any appropriate chemistry—even though such moieties or agents can have polymeric components.

physiological pH means a pH between 6.5 and 7.5.

polyanionic polymer means a polymer having an acyclic backbone and having ionizable functional groups, for example carboxy groups, that become negatively charged functional groups, for example carboxylate anions, at physiological pH. A gram of polyanionic polymer has 0.001 moles or more of functional groups that can be titrated with KOH. The ionizable functional groups can be directly chemically bonded to the polymer backbone or they can be chemically bonded to a side group or side chain that is in turn chemically bonded to the main chain. Carboxypolymethylene is an example of a polyanionic polymer in which the ionizable functional group is directly bonded to the main chain. α-Poly(glutamic acid) is an example of a polyanionic polymer in which the ionizable functional group is bonded to a side group that is an ethylene group. A polyanionic polymer segment is a linear polymerization product that is incorporated into a larger polymer via crosslinks; each such segment meets the definition for polyanionic polymer.

pre-formed polymer is a polymer that is chemically formed ex situ, prior to administration to a subject.

The linking agents or linking moieties of the invention can be obtained via a variety of approaches, such as those detailed below. Generally, most of the linking agents or linking moieties are used to create polymers according to the following:

Approach I: Formation of degradable cross-linked PAP during free-radical polymerization.

Carbomers are formed presently by polymerization of acrylic acid in the presence of a degradable crosslinking agent. The contributions of this Approach I come by design of linking moieties to yield hydrolytically degradable hydrogels. One or more hydrolytically susceptible links are placed within the crosslinking agent, e.g. between the sites of polymerizable unsaturation. This is contrasted with the crosslinking agent that is used in commercial Carbomers, (1), which is designed to be hydrolytically stable:

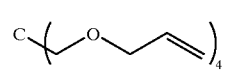

(1)

In these polymers, it may be advantageous to polymerize the anionic monomers under conditions that the PAP MW is relatively low, approximately 50,000 and less, for example, using chain transfer agents or with high concentrations of initiator.

I.A.: Degradable linking moieties based on pentaerythritol cores:

To achieve degradability, one seeks to incorporate bonds that are known to be hydrolytically susceptible within the linking moiety, such as esters, amides, carbonates, ureas and the like. For example, one can incorporate (2), which can be prepared by reaction of pentaerythritol with acryloylchloride:

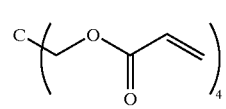

(2)

A linking agent that contains both a carbonate and an ester, which can be expected to degrade faster than (2), can be prepared from pentaerythritol and hydroxyethylacrylate linked with phosgene:

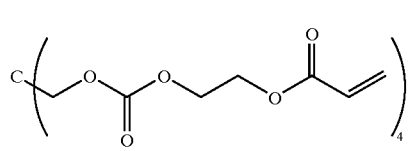
(3)

Naturally, the above can be made from a variety of cores, such as 1,2-ethanediol, or from glycerol, or from triethanolamine, or from other cores that can be identified by those skilled in the art.

I.B.: Degradable linking moieties based on two or more unsaturated sites of polymerization, for example, materials from hydroxyethylacrylate (4) and/or aminoethylacrylate (5):

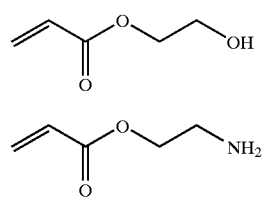
(4)

(5)

For example, dimerization of (4) and (5) with phosgene will yield at least one of the following, depending on the dimerized pair:

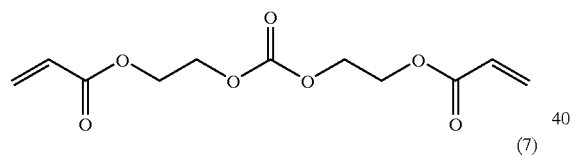
(6)

(7)

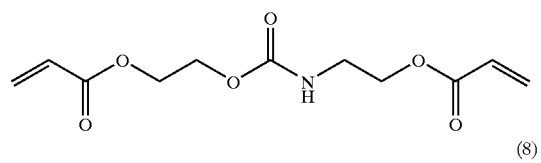

(8)

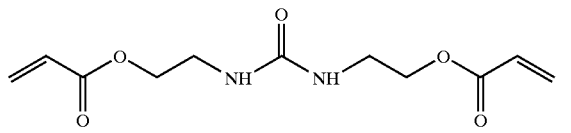

One can expect (6) to degrade faster than (7), and (7) to degrade faster than (8). One can make analogous structures with more than two unsaturated sites of polymerization.

I.C.: Degradable linking moieties based on materials from acryloylchloride (9):

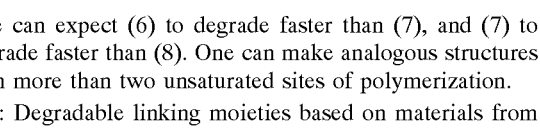
(9)

Dimerization of (9) with 1,2-ethanediol yields (10), which is hydrolytically susceptible:

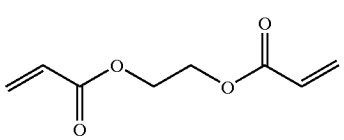
(10)

Dimerization of (9) with ethanolamine yields (11), which can be expected to degrade slower than (10):

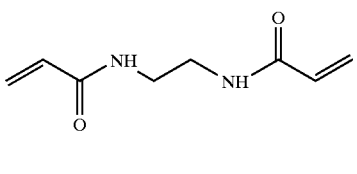
(11)

Dimerization of (9) with 1,2-diaminoethane yields (12), which can be expected to degrade slower than (11):

(12)

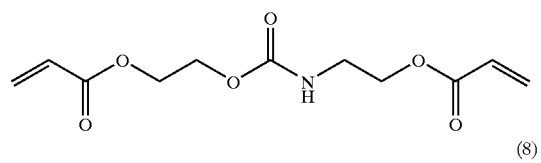

Alternatively, one can form the anhydride crosslinking agent, which can be expected to degrade faster than (10):

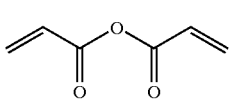
(13)

I.D.: Degradable linking moieties based on lactic acid or other hydroxy acids:

I.D.1.: One can react lactic acid (14)

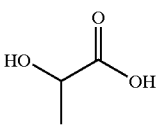
(14)

with acryloylchloride to form (15):

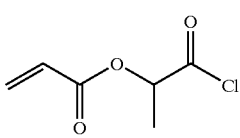
(15)

(15) can then be reacted with hydroxyethylacrylate to form (16):

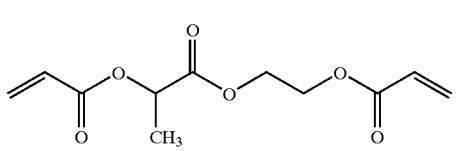
(16)

One can make such structures with more than two unsaturated sites of polymerization as well.

I.D.2.: One can also use lactyl esters, i.e. dimers of lactic acid, or dimers of other hydroxy acids. For example, one can take hydroxyethylacrylate and employ the hydroxyl to ring open lactide under non-polymerizing conditions to yield (17):

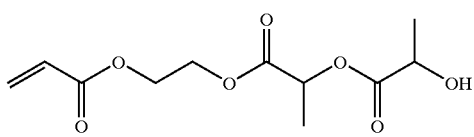
(17)

17) can be reacted with acryloylchloride to form the linking agent (28):

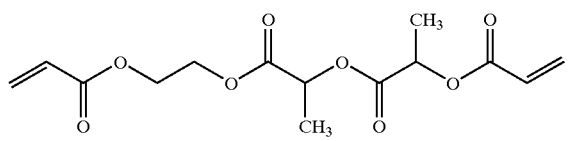
(18)

Like structures can be formed with more than two unsaturated sites of polymerization and with other hydroxy acids.

I.E.: Linking agents containing PAO diols (19) or other multifunctional PAOs, or other difunctional or multifunctional water soluble polymers, of which PEG is exemplary, as illustrated in a number of exemplary structures below:

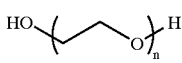
(19)

Such approaches are advantageous in that the MW of the PAO can be altered to gain a second approach to control of the physical characteristics of the hydrogel particles. Higher MW PAOs yields lower degrees of cross-linking.

I.E.1.: With PAO diols:

One can form the carbonate-containing linking agent by linking PAO to hydroxyethylacrylate with phosgene, to obtain (20):

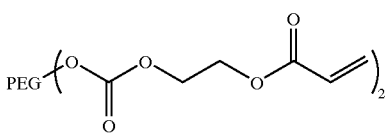
(20)

Alternatively, the ester-containing group can be obtained by reacting PAO with acryloylchloride to obtain (21)

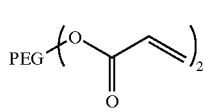
(21)

One can incorporate lactic acid esters such as be reacting PAO diol with lactic acid and phosgene to form (22):

(22)

The acid chloride of (22) is formed and reacted with hydroxyethylacrylate to obtain (23):

(23)

One can activate the hydroxyl of PAO diol to form an ester with lactic acid (24):

(24)

(24) is then reacted with acryloylchloride to obtain (25):

(25)

One can alternatively link a pair (or more) of lactic acid residues, by a ring-opening reaction with lactide to obtain (26):

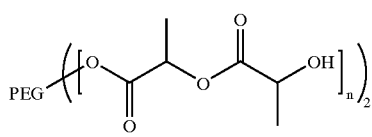
(26)

where n is preferably 10 or less, more preferably 5 or less. (26) can be acrylated to yield (27);

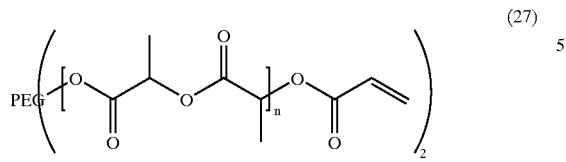

Alternatively, one can couple (26) to hydroxyethylacrylate to obtain (28):

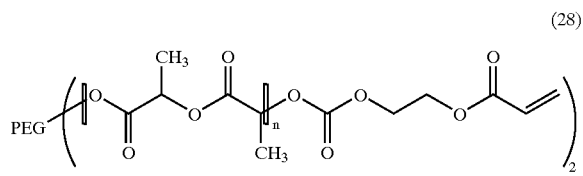

I.E.2.: Polymers made with PAO diamines:
Analogous amide and urea structures can be obtained from PAO diamine. In general, these structures will degrade more slowly than their ester and carbonate analogues.
Approach II: Linking or cross-linking of shorter PAP chains with PAO chains, employing a degradable linker between the two:
The polymerization of PAP chains in the absence of cross-linking, and then cross-linking them thereafter, provides facile control over PAP MW and thus over the pharmacodynamics of the degradation products of the cross-linked polymer particles.
II.A.: Polymers made from poly(AM-co-hydroxyethylacrylate):
Small amounts of hydroxyl can be included along the PAP chain, for example, by co-polymerization of anionic monomer with hydroxyethylacrylate ($H_2C\!=\!CHCO_2CH_2CH_2OH$) or by copolymerization with vinyl acetate, followed optionally by then hydrolysis of the acetyl side group to yield the additional alcohol. The hydroxyl side groups can be cross-linked by reaction with PAO diol activated with phosgene to yield (29):

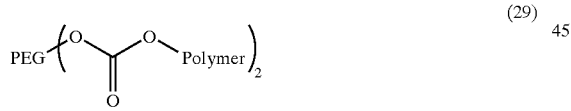

II.B.: Polymers made from PAP:
Alternatively, one can begin with PAP, derivatize some of side-chain carboxyl groups (or analogous groups) with aminoethane thiolgroups, and cross-links these with a degradable diacrylate linking agent, for example, (21) to yield (30):

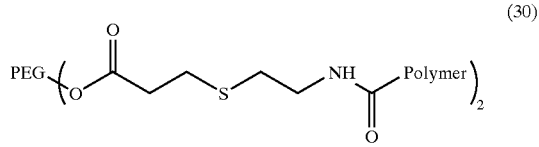

II.C.: Polymers containing both carbonate and ester links:
One can start with PAP, convert some of the carboxyl side groups (or analogous groups) to the acid chloride, and functionalize these with 1,2-ethanediol under non-cross-linking conditions. This material can be cross-linked with PAO diol that has been pre-activated with phosgene, to yield (31):

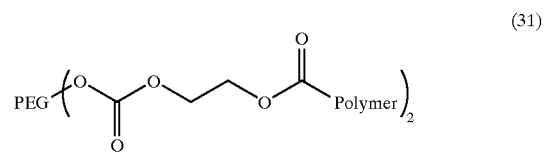

(31) can also be formed from the copolymer with hydroxyethylacrylate and then coupling with PAO after activation of the PAO with phosgene.

II.D.: One can incorporate lactic acid, or other hydroxy acids, in the linkers from the hydroxyl-containing copolymer (shown here from the hydrolysis product of a copolymer with vinyl acetate) after ring opening of lactide under non-polymerizing conditions to obtain (32):

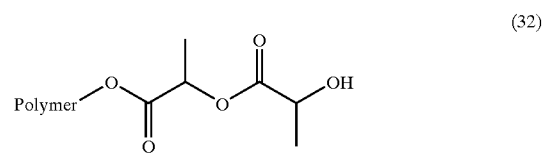

(32) can then be coupled with phosgene-activated PAO diol to obtain (33):

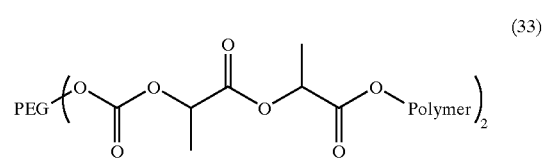

One can also use the PAO terminal hydroxyls to ring open lactide under non-polymerizing conditions to yield a diol precursor and couple this to phosgene-activated PAO diol to obtain (34):

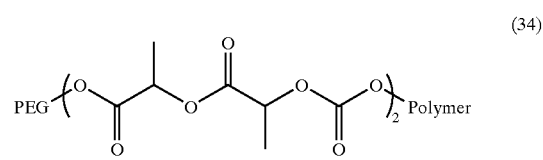

Approach III: Cross-linking of PAP:

As in Approach II, one can cross-link or link PAP after polymer-forming reaction.

III.A.: For example, one can start with PAP, form a small fraction of the acid chloride, and cross-link with 1,2-ethanediol, or a similar diol, to obtain (35):

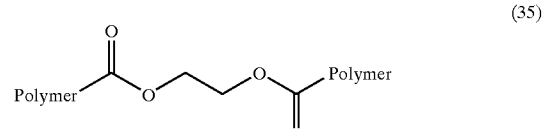

III.B.: One can start with a hydroxyl-containing copolymer and cross-link with phosgene, to obtain (36):

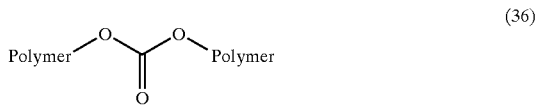

(36)

Alternatively, the anhydride linked material may be obtained directly (37)

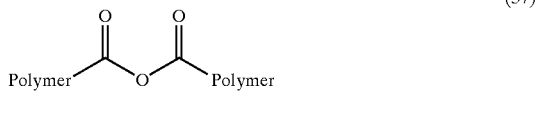

(37)

III.C.: One can use a lactide ring-opening reaction, for example, with 1,2ethanediol in excess, to obtain (38):

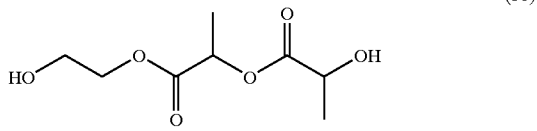

(38)

(38) can be used to cross-link a phosgene-activated homopolymer to obtain (39) or with an acid-chloride activated homopolymer PAP to obtain (40):

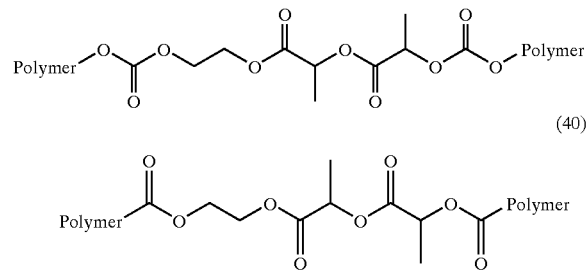

(39)

(40)

Approach IV: Hydrolytically susceptible (i.e., unstable) linear PAP.

Coupling of short PAP chains via degradable moieties can be used to obtain a linear PAP with a high molecular weight.

IV.A.: Degradable linear PAP from hydroxyl terminated PAP.

One can polymerize anionic monomer via living polymerization and obtain low molecular weight PAP with terminal hydroxyl groups (41):

(41)

Coupling of the hydroxyl groups with phosgene results in an extended PAP chain linked by degradable carbonate groups (42):

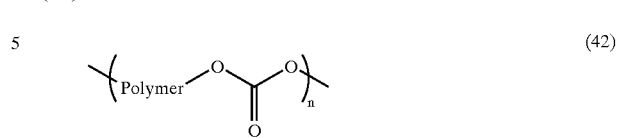

(42)

The size of the degradable block can be increased by reaction of hydroxyl terminated PAP with, for example, a PAO diol, activated by phosgene to yield (43):

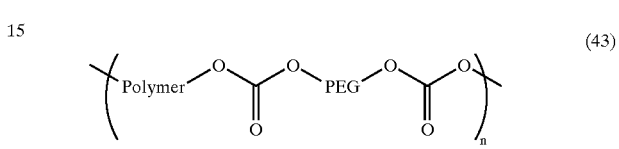

(43)

One can also use (41) in a lactide ring opening reaction under non-polymerizing conditions to obtain (44):

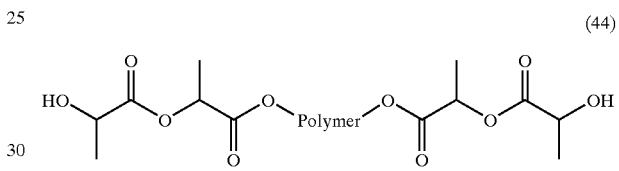

(44)

Subsequently, the hydroxyl groups of 2 such polymer segments can be reacted with 1,1'-carbonyldiimidazole (CDI) (or phosgene can be used) to obtain a high molecular weight PAP composed of PAP blocks separated by lactyl moieties, for example, (45):

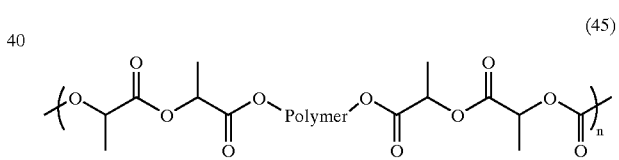

(45)

Alternatively, (44) can be coupled to (41) in this way, yielding (46):

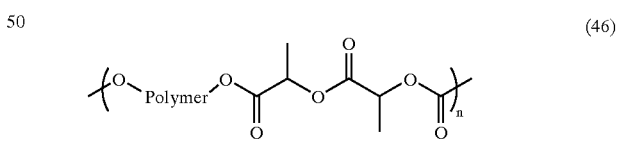

(46)

IV.B.: Degradable linear PAP from PAP segments.

As in IV.A, one can obtain low molecular weight PAP via living polymerization with other terminal groups than hydroxyl groups, for example, thiol groups (47)

(47)

These groups can be reacted with diacrylated compounds, as described in II.B, for example, with a PAO-diacrylate (21) to obtain (48):

(48)

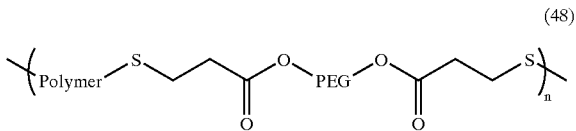

Reacting (47) with shorter degradable blocks, for example, diacrylates(10), (11), and (12) from I.C., one can expect to obtain polymers (49), (50), and (51) with different degrees of degradation susceptibility:

(49)

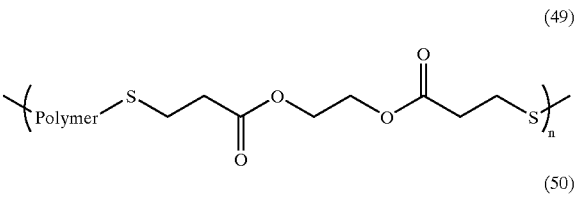

(50)

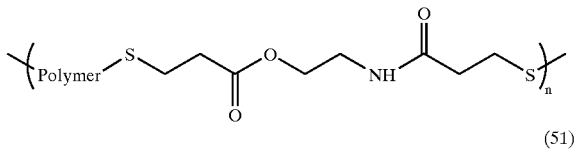

(51)

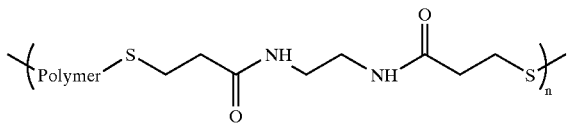

Polymer Compounds

In some embodiments, the backbone, or main chain, of polyanionic polymers of the invention includes repeat units that can be derived from polymerization of one or more monomers, including preferably monomers of structure I, wherein the double bond shown is disposed to polymerization at least by free radical polymerization.

In structure I, $R^1$, $R^2$, and $R^3$ can be independently selected from, hydrogen, alkyl having 1 to 6 carbon atoms (a $C_1$–$C_6$ alkyl group), carboxy, halogen, cyano, isocyanato, hydroxyalkyl, alkoxyalkyl, haloalkyl, cyanoalkyl, cycloalkyl, carboxyalkyl, aryl, hydroxyaryl, haloaryl, cyanoaryl, carboxyaryl, or $R^1$, $R^2$, and $R^3$ can also be a group —X—Y, as these structures are defined below. The alkyl and alkoxy groups in the foregoing list may be linear or branched and preferably have from one to six carbon atoms. The cycloalkyl group preferably has five or six carbon atoms, one or more of which can be independently replaced with O, S, or N heteroatoms such that up to Q-2 carbon atoms of the cycloalkyl group (Q being the total number of carbon atoms in the cycloalkyl ring) can be replaced with heteroatoms.

In structure I, X is a direct bond or is a straight or branched alkylene group, preferably having two to six carbon atoms, one or more of which can be replaced with O, S, or N heteroatoms, provided that there is no heteroatom in a position α or β to Y. In structure III, X can also be phenylene, preferably 5 or 6 membered arylene having up to two heteroatoms independently selected from O, S, and N, with the proviso that Y and $R^3R^2C=C(R^1)$— are not bonded to a heteroatom. Phenylene, oxazolylene, isoxazolylene, pyridazinylene, pyrimidinylene are examples of preferred arylenes.

In structure I, Y is —C(O)OR$^4$; —O—S(O$_2$)R$^4$, —S(O$_2$)R$^4$, —S(O)OR$^4$; wherein $R^4$ is hydrogen or a cleavage permitting group, such as lower alkyl, especially $C_1$ to $C_6$ alkyl (branched or unbranched), phenyl, or benzyl. The group Y can be present in the monomer or the monomer can include a precursor group for Y, which is then formed in a post-polymerization reaction on polymer formed from monomer having the precursor group. By way of example, a polymer having methyl carboxylate groups, derived for example from methyl methacrylate, can be reacted with water and to produce a polymer having carboxy groups (Y=—COOH).

In the above structure, aryl means phenyl or a 5 or 6 membered heteroaryl group having up to Q-2 heteroatoms independently selected from O, S, and N; wherein Q is the total number of atoms in the ring.

Examples of suitable monomers include acrylic acid, methacrylic acid, allyl sulfonic acid, itaconic acid, maleic acid or its anhydride, itaconic acid, citraconic acid, to mention a few. Many other monomers that can be used to make polyanionic polymers that form microgels with water are described by Huang et al., U.S. Pat. No. 4,509,949.

In reference to crosslinked polyanionic polymers that can form microgels, the term backbone and main chain are used interchangeably and will be understood to refer to that portion of the polymer chains not derived from linking moieties.

In some embodiments, the microgel has a particle size between 1 and 500 μm in its aqueous swollen state at a pH between 6 and 8. In other embodiments, the microgel has a particle size between 10 and 500 μm in its aqueous swollen state at a pH between 6 and 8.

The polyanionic polymers used in the method of the invention can be homopolymers, having repeat units derived from only one monomer described by structure I, or they can be multipolymers derived from polymerization of a mixture of any number of monomers of structure I. Co-, ter-, quatra-, and other multipolymers can include repeat units from monomers that do not bear ionizable groups or precursors therefor, for example styrene, that are capable of copolymerizing with the monomers of structure I, with the proviso that the final polymer preferably has 0.001 or more moles, preferably 0.0014 or more moles, more preferably 0.01 mole or more, of base titratable functional groups per gram of polymer (on a commercially acceptable dry basis). A base titratable functional group is a functional group, for example a carboxy group, that can be titrated with KOH.

It will be appreciated that the compounds of the invention can be synthesized according to a variety of synthetic steps with reactants other than those discussed herein, which variations are well known in the art at the time of filing. Polymers of the invention can be synthesized by a mechanisms including addition and condensation reactions. In some embodiments, polymer synthesis can be accomplished by living polymerization. Living polymerization can include the growth of a polymer chain that remain reactive until a reagent is added to quench the reaction. An example of a reaction that can be carried out as a living polymerization is the polymerization of an alkene monomer with an anionic reactive species. In this example, the reactive species can have one or more reactive anionic sites that will react with the alkene monomer but not with each other. In contrast, reactive radical sites in a free radical polymerization process can react with each other to terminate a reaction. A possible consequence of the living polymerization, where active centers can be initiated at the same time, react at the same rate and are quenched at the, is that polymer chains synthesized by this process are generally characterized by narrower molecular weight distributions and more uniform chain lengths, a greater potential to remain reactive until quenching.

In some embodiments, polymer synthesis can be accomplished by addition reactions via stepwise addition of monomer units to a growing polymer chain at an active center (for example, a cation, anion or free radical) of a reactive intermediate species. In some embodiments, polymer synthesis can be accomplished by condensation reactions between reactive polymer species which can be monomers or reactive polymers of any chain length. For example, amide and ester functional groups in polymer chains can be synthesized by condensation reactions.

Polymers of the invention may be isotactic, syndiotactic or atactic. Control of the stereochemistry of chiral centers in the polymers of the invention can be accomplished by selecting appropriate synthesis conditions and methods, as known in the art. For instance, use of a Ziegler-Nata catalyst is one method known in the art to produce polymers stereospecifically. The addition of plasticizers to modify the polymers of the invention is also within the scope of the invention. In some embodiments, where applicable, polymers of the invention can be structurally modified during synthesis, within the scope of the inventive compounds, so as to change the physical properties of the polymer such as the glass transition temperature.

In preferred embodiments, polyanionic polymer is crosslinked and forms a microgel when combined with water. Preferred crosslinked polyanionic polymers are chemically crosslinked. Chemical crosslinking can be by ionic or covalent bonds, preferably it is by covalent bonds. The crosslinking can be introduced at the time the polyanionic polymer is made, or it can be introduced after the polyanionic polymer is made. The chemical crosslinks can be durable under physiological conditions or they can be labile under physiological conditions. With respect to crosslinks, labile means susceptible to enzymatic or nonenzymatic hydrolysis or oxidation.

Preferably, crosslinking by covalent bonds is introduced at the time the polyanionic polymer is made by using one or more chemical linking moieties that have at least two ethylenically unsaturated carbon-carbon double bonds disposed to polymerize by the same mechanism as the monomers represented by structure I, preferably a free radical mechanism. Chemical linking moieties introduced at the time the polyanionic polymer is made can be selected to result in covalent links that will be durable under physiological conditions after application of a composition containing a polyanionic polymer. That is, the links introduced by the linking agent resist break-down or scission under physiological conditions. Examples of linking moieties that can be introduced at the time the polyanionic polymer is made and that result in durable crosslinks include divinyl benzene and alkenyl ethers of polyhydric alcohols, for example the triallyl ether of pentaerythritol available from Aldrich Chemical (catalog 25-172-0), among others. Commercially available ethylenically unsaturated ethers or esters of those polyhydric alcohols having 3 or more hydroxyl groups typically are provided as a mixture in which some of the hydroxyl groups may be underivatized. Reference herein to a particular degree of etherification or esterification, for example tri- or tetra-, will be understood to also refer to commercially important mixtures of etherified or esterified polyhydric alcohols as are known in the art to include minor amounts of etherified or esterified polyhydric alcohols having a lower or higher than indicated degree of etherification or esterification. Thus, reference to a particular mole fraction of double bonds will be understood to encompass the variation expected because of this known variation in the degree of derivatization.

In one embodiment, the crosslinked polyanionic polymers of the invention can be made by any method that provides a crosslinked polymer having an acyclic backbone and functional groups capable of ionizing to an anionic form under physiological conditions. For example, the polyanionic polymers used in the method of the invention can be obtained by polymerization of a mixture that includes an ethylenically unsaturated linking agent and at least one monomer that has an ionizable functional group capable of becoming negatively charged. Typically, the ionizable functional group is a base-titratable functional group. The carboxy group is an example of a base titratable functional group. The polyanionic polymer can also be obtained from a precursor polymer having precursor functional groups that can be hydrolyzed to the ionizable functional groups that, in turn, can become negatively charged. For example, a carboxylate ester is a precursor for a carboxy group which, when treated with base, becomes a negatively charged carboxylate anion. The precursor polymer can be obtained by polymerization of a mixture that includes one or more monomers at least one of which has a precursor for a functional group that is capable of becoming negatively charged. The precursor group can be converted to the functional group capable of becoming negatively charged by, for example, hydrolysis, or any other means as will be obvious to one skilled in the art from inspection of the chemical structure of the precursor group. Conversion of the precursor group can be made to occur prior to, at the time of, or after administration of a composition of the invention.

Without being limited to theory, break-down of the crosslinks is believed to facilitate eventual elimination of the polyanionic polymer from the animal being treated because fragments of reduced molecular size (molecular weight) are formed when the crosslinks break down and the smaller fragments are more easily eliminated (Yamaoka et al., J. Pharm. Sci, 84, 349(1995)). Break-down of the crosslinks is facilitated if the two or more ethylenic double bonds of the linking agent are separated by functional groups, for example esters or amides, that are disposed to hydrolysis. Examples of linking moieties having ester linkages include acrylates and methacrylates of dihydric and polyhydric alcohols such as ethylene glycol, diethylene glycol, pentaerythritol, glycerol, and sorbitol. Such linking moieties are either commercially available (for example, pentaerythritol triacrylate, Aldrich Chemical catalog 24,679), or can be readily prepared from the polyhydric alcohol and acryloyl or methacryloyl chloride. Acrylates and methacrylates of polyethylene glycols having molecular weights between 200 and 40,000 can also be used as linking moieties. Ethylenically unsaturated derivatives of oligosaccharides, or their reduction products, can be used as crosslinkers. A particularly preferred linking agent of this type is allyl sucrose. Linking moieties in which there is at least one carbonate or carbamate group between each ethylenic double bond and any other ethylenic double bond of the linking agent can also be used. Bis-(2'-acryloxyethyl) carbonate, pentaerythritol tri(2'-acryloxyethyl)formate, and N-(2-acryloxy)ethyl-(2-acryloxy)ethyl carbamate are examples of carbonate-linked and carbamate-linked linking moieties. Crosslinked polyanionic polymers having labile crosslinks can also be prepared with linking moieties in which the ethylenic double bonds are linked by urea groups. N,N'-di(2'-acryloxyethyl) urea is an example of a urea-linked linking agent. Linking moieties based on lactic acid can also be used. 1-(2-acryloxypropanoyl)2-acryloxy ethane is an example of such a linking agent.

Crosslinking by non-durable covalent bonds can be introduced after the polyanionic polymer is made by functionalizing the polyanionic polymer and reacting it with a suitable linking agent. For example, when Y of structure I is a carboxyl group, from 0.1% to 10% of the carboxyl groups in the polymer can be functionalized to the acid chloride by, for example, the action of thionyl chloride. The acid chloride groups so formed can be reacted with, for example, an $\alpha$, $\omega$-diamine or $\alpha$, $\omega$-diol, for example a polyethylene glycol, to form covalent crosslinks through amide respectively ester groups on different polymer chains. Crosslinking can also be introduced after the polyanionic polymer is formed by providing pendant hydroxyl groups on the polyanionic polymer and reacting these with a bischloroformate, for example the bischloroformate of an $\alpha$, $\omega$-diol. The polyanionic polymer can be provided with pendant hydroxyl groups by polymerizing one or more monomers of structure I with vinyl acetate, followed by hydrolysis of the acetate groups, or by copolymerizing one or more monomers of structure I with, for example, hydroxyethylmethacrylate (HEMA). Generally, the amount of vinyl acetate or HEMA copolymerized will be sufficient to provide 0.1 to 10 hydroxyl groups per 1000 repeat units on a moles basis.

Preferably the amount of crosslinker is kept low. Preferred crosslinked polyanionic polymers form microgels with water and are made by polymerization of a mixture of one or more monomers of structure I and one or more ethylenically unsaturated linking moieties of the type discussed above. The amount of linking agent or agents used is effective to produce a crosslinked polyanionic polymer that forms a microgel when combined with water. When ethylenically unsaturated linking moieties are used to form crosslinks at the time of making the polyanionic polymer, the ethylenic double bonds of the one or more ethylenically unsaturated linking moieties preferably account for less than 0.02 mole fraction and preferably less that 0.01 mole fraction of all ethylenically unsaturated double bonds in the combination of one or more monomers and one or more linking moieties. Typically, the ethylenically unsaturated linking agent account for 0.001 mole fraction or more of all ethylenically unsaturated double bonds in the combination of one or more monomers and one or more linking moieties. These mole fractions are calculated on the basis of the nominal number of ethylenic double bonds in the ethylenically unsaturated linking agent and are adjusted for the known variation in the average number of double bonds per molecule of commercially available ethylenically unsaturated linking moieties as discussed above.

The hydrolytically susceptible polymers of the invention are preferably prepared so that the distribution of hydrolytically susceptible bonds is designed to provide that hydrolysis of these bonds reduces the molecular weight of the polymers to ½, ¼, ⅛ or less of the original molecular weight.

In certain embodiments, the polyanionic polymer employed in the practice of the method of the invention has an acid number of at least about 100, more preferably at least about 200, yet more preferably at least about 400, still yet more preferably at least about 600, still more preferably at least about 700, when the polymer is in a commercially acceptable "dry" preparation such as a preparation containing the polymer and for example up to 2% moisture, residual solvent, or residual monomer. In preferred embodiments, the polyanionic polymer has 0.001 moles or more, preferably 0.0014 moles or more, more preferably 0.014 moles or more, of base titratable functional groups per gram of polymer in a commercially acceptable dry formulation.

The polyanionic polymers preferably have, in a 0.5% w/v neutralized aqueous solution (for example, pH between 6 to 8), a Brookfield RVF or RVT viscosity, which is a measure of macroviscosity, of at least about 2,000 cP, more preferably at least about 4,000 cP (20 rpm at 25° C.). These viscosity parameters are with respect to the acid form of the polymers. See, R. Y. Lochhead et al., *Polymers in Aqueous Media,* pp. 113–147, 1989 on macroviscosity (Brookfield viscosity) and microviscosity of polymer solutions. However, in certain preferred embodiments, the macroviscosity is no more than about 100,000 times greater than the microviscosity, preferably no more than about 10,000 times greater.

In certain embodiments, the crosslinked polyanionic polymer is analogous to a crosslinked homopolymer or copolymer of anionic monomer, such as the polymers sold by the BFGoodrich Company, Specialty Polymers and Chemicals Division (Brecksville, Ohio) under the tradename Carbopol, such as carbopol 971P, Carbopol 934P and : Carbopol 974P, which are preferred in the order: 971P more than 934P; and 934P more than 974P. These types of polymers have a substantially acyclic aliphatic backbone and have been termed carboxypolymethylenes or carbomers, which can be composed of any suitable number of monomers, and in a particular treatment, can be of a uniform number of such monomers or of a variable number of monomers per preparation applied to an area affected by a wound. Additionally, carboxypolymethylene can have a variable number of carboxyl groups attached to the polymethylene backbones. As crosslinker, the triallyl ether of pentaerythritol (at 0.1% to 2.5% ,w/w, based on other monomers) is suitable.

Suitable salts can be combined with a microgel, the suitability of which is determined by the requirement that the microgel itself not cause harm to the injured cornea, peritoneum, or any other tissue with which the microgel comes in contact. Suitable salts include, but are not limited to, potassium or sodium chloride, particularly when provided at physiological concentrations, as are known in the art.

A composition used in the practice of the method of the invention can include glycerol, the aforementioned carboxypolymethylene, and distilled water. The composition can be pH adjusted using a base such as sodium hydroxide potassium hydroxide, alkyl amines such as diisopropanolamine (DIPA), and the like. A stock solution of a suitable concentration of glycerol can be prepared with distilled water, and is preferably an 87% (w/w) glycerol solution, the remainder of which is distilled water. A stock solution of a suitable solution of base such as sodium hydroxide can also be prepared with distilled water, for example, a 10% (w/w) sodium hydroxide solution, the remainder of which is water. By making appropriate dilutions of stock solutions, as is well known in the art, the microgel useful in the practice of the present method preferably has the following ranges of end concentrations of the aforementioned ingredients: (1) glycerol, from about 0 to about 60% (w/w); (2) carboxypolymethylene, from about 0.1% to about 10% (w/w), more preferably from about 0.4% to about 7%, yet more preferably, from about 1% to about 5%; the remainder of the formulation being distilled water. Sodium hydroxide, 10% stock, is used for pH adjustment, resulting in an to essentially neutral prepared pH, more preferably a pH from about 7 to about 7.8, yet more preferably a pH from about 7.2 to about 7.6.

The compositions used in the context of the method of the invention are useful, for example, for topical application with respect to an area to be so treated. Alternatively, systemic and oral modes of treatment are contemplated as well. Microgels can be applied as paste, jelly, or in sheets that can be prehydrated or hydrated in situ by bodily fluids.

Certain Linking Moieties

In one embodiment of the invention, (a) a core which is a $C_1$ to $C_{12}$ (preferably $C_1$ to $C_{10}$ or $C_1$ to $C_5$) alkylene with three or more (e.g., up to 5 or 6) linking hydroxyls or thiols or a mono or disaccharide with three or more linking hydroxyls is reacted with (b) three or more (e.g., eight) equivalents of a cyclic diester of the following formula:

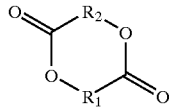

(52)

in which $R^1$ and $R^2$ are independently methylene or ethylene which can be substituted with up to two $C_1$ to $C_4$ alkyls. The resulting multivalent core has a structure with substituents at the former hydroxyls or thiols which are $-R^3{}_n$, where n is zero or more (such as zero to eight) with the total sum of the n values being at least three to eight (such as three to eight), and $R^3$ is independently:

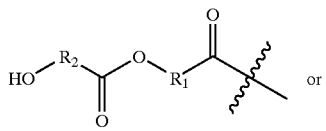

(53)

or

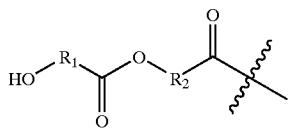

(54)

Preferably, $R^1$ and $R^2$ are methylene, which can be substituted. Preferably, the substitution is $C_1$ to $C_2$ alkyl. The terminal hydroxyls from the opened cyclic diester are reacted to substitute the hydroxyl with an ester or ether-linked unsaturated moiety adapted to be reactive in a subsequent free-radical polymerization (which in turn is adapted to yield polyanionic polymer segments). Preferably, this moiety is a ester-linked acryloyl radical, as can be formed for example with acryloylchloride. The average of n is preferably 1 or 2. Preferably, at least 80%, 90%, 95% or 98% or more of the of the linking hydroxyls or thiols of the core are so reacted. One preferred core is pentaerythritol.

Starting with any multivalent core (such as any described in any section of this specification) having terminal unsaturated moieties adapted to be reactive in a subsequent free-radical polymerization, the subsequent free radical polymerization is preferably adapted to limit (e.g., with a chain terminator) the polyanionic polymer segments to molecular weights for 90% or more of the segments of 50 kd or 40 kd or less. In one embodiment, 95%, 98% or more of the segments fall within these size limits. Preferably, the average molecular weight is from 20 kd to 40 kd, or 25 kd to 35 kd. Appropriate chain terminators are known in the art.

Thus, in one embodiment of the invention, the polyanionic polymer has polyanionic segments of these sizes crosslinked with multivalent crosslinkers containing hydrolytically susceptible bonds.

Core moieties can be reacted with compounds of formula (52) at an elevated temperature effective to melt such compounds of formula (52), such as 120° C. for lactide, and the reaction conducted over, for example, an 20 or more hours. An example of forming the linked moieties adapted to be reactive in a subsequent free-radical polymerization is reacting with acryloylchloride in dichloromethane in the presence of triethylamine at ambient temperature.

Other preferred hydrolytically susceptible polymers polyanionic polymers include any in which comprise two or more linearly linked polyallionic segments where the linkages are through hydrolytically susceptible linking moieties connecting to terminal oxo or thio moieties of the polyanionic segments, such as those described above under Approach IV. Preferably, the segments fall within one or more of the size restraints described here. These linear multimers of polyanionic segments can be further crosslinked with liydrolytically susceptible linking moieties.

In other preferred hydrolytically susceptible polymers polyanionic polymers, containing carboxylates, for which a sampling of the carboxylate-providing monomers (e.g., 1 of 20) are derivatized to attach $-X-R^4-Y-H$ via an amide, ester or thioester bond, where X and Y are independently S, O or NH and $R^4$ is a straight chain $C_1-C_{10}$ (preferably $C_1-C_5$) alkyl which can be substituted with up to two $C_1-C_4$ alkyls. Preferably, X and Y arc different to provide differential reactivities that facilitate selective addition of one end to the polyanionic polymer. However, protecting group chemistry (see illustrations in copending Ser. No. 09/644, 022) can be used to achieve this selective attachment even if X and Y are the same. YH in turn reacts by Micheal addition with a crosslinkers (linking moieties) with terminal acrylate or acrylamide moieties. Thus, the linking moiety has the structure:

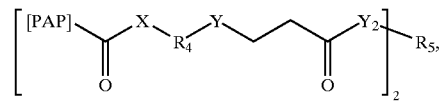

where $y^2$ is S, O or NH (preferably O or NH), n is 2 or more (e.g., up to 4, 5 or 6) and $R^5$ is an hydrolytically susceptible linking moiety comprising C, H and two or more heteroatoms which can be O,S or N, the O, S and N atoms all participating in hydrolytically susceptible bonds or ether or thioether bonds. $R^5$ can be or include a segment of PAP (such as PEG), which preferably has molecular weight within the above-described preferred ranges. Aside from PAP, which may not be present, $R^5$ preferably has molecular weight of less than 5,000, more preferably less than 1,000. A large number of examples of $R^5$ are described herein.

Certain Other Linking Moieties

Linking moieties comprise the groups identified above, for which synthetic chemistries are identified in the discussion below.

In some embodiments, linking moieties of the invention can comprise the following groups:

A

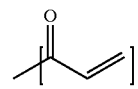

B

D

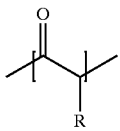

D'

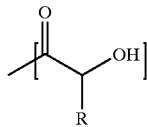

E

wherein lines extending outside the square brackets indicate points of attachment to adjacent moieties, wherein n is an integer between 1 and 6 and wherein R is a ($C_1$–$C_6$) alkyl, alkenyl or alkynyl chain being straight or branched, and optionally substituted with one or more heteroatoms selected from the group consisting of S, N and O. Additionally, linking moieties or linking agents of the invention can comprises "$C_n$", which represents n repetitions of an $C_1$ to $C_4$ alkylene group.

In some embodiments, linking moieties of the invention can be written according to the following formulas, wherein A, B, $C_n$, D, D' and E are defined above and X, X', X", Y, Y', Y" and Y'" are independently S, N or O. In one embodiment, compounds of the invention can be written according to formula II:

II

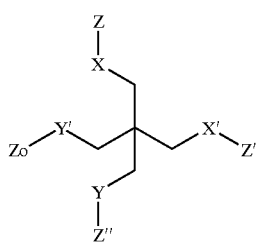

wherein X, X', Y and Y' are defined above, and $Z_o$, Z, Z' and Z" are independently A, B or E-Y-Cn-Y'-B.

In some embodiments, linking moieties of the invention can be written according to the following formulas, wherein A, B, $C_n$, D, D' and E are defined above and X, X', X", Y, Y' and Y" are independently S, N or O. $C_n'$ is defined as $C_n$ above, but is independent of $C_n$ in chain length.

B-X—$C_n$—X'-E-Cn'-Y-B

B-X—$C_n$—X'-B

B-X-B

B-X-D-X'—$C_n$—Y-B

B-X—$C_n$—X'-D-Y-D'

B-X—$C_n$—X'-D-Y-B

B-X—$C_n$—X'-D-Y-D'-Y'-B

In some embodiments, linking moieties of the invention can be written according to the following formulas, wherein A, B, $C_n$, D, D', X, X', X", Y, Y' and Y" are defined above; wherein Y'" can be O, S or N; wherein n, m, q and r are independently integers of 0, or 1 or greater; wherein P is any polymer described in the invention; and wherein Z and Z' are independently functional groups of one of the following formulas and whereby X is bonded to the body of the polymer chain in formula III:

III

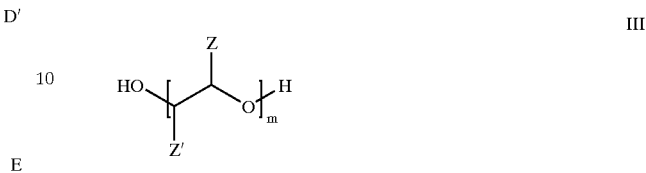

wherein Z and Z' are independently selected from the group consisting of:

-X-E-Y-Cn-Y'-B

-X-B

-X-E-Y-D'

-X-E-Y-D-X'—$C_n$—X"-B

-X-D'

-X-D-Y-B

-[X-D-Y-D]$_r$OH

-[X-D-Y-D]$_r$X'-B

-[X-D-Y-D]$_r$Y—$C_n$—Y'-D'

-X-E-Y-P

-X-E-Y—$C_n$—Y'-E-P

-X-E-X'-D-Y-D-Y'-P

-X-E-Y-D-X'-D-Y'-E-X"-D-Y"-D-Y'" -P

-X-D-Y-D-X'-E-Y'-P

In some embodiments, linking moieties of the invention can be written according to the following formulas, wherein A, B, $C_n$, D, D', X, X', X", Y, Y', Y", Y'", P, m, n, q or r are as defined above, wherein HO is a terminal hydroxymethyl group and wherein P' is any polymer described in the invention:

P-X-D-Y-D'

P-E-X-Cn-Y-E-P'

P-X-E-Y-P'

P-E-X-E-P

HO—$C_n$—X-D-O-D'

P-X-Cn-X'-D-Y-D'

P-X-E-X'-Cn-X"-D-Y-D-Y"-E-Y'"-P

P-E-X-Cn-X'-D-Y-D-Y'-E-P

X-P-Y

-[P-X-E-Y-]$_r$

-[(P-X-E-X')$_q$—Y-Cn-Y'-E-X"]$_r$—,

D'-X-D-X'-P-Y-D-Y"-D'

-(X-D-X'-D-X"-P-Y-D-Y'-D-Y"-E)$_r$—

-(X-P-Y-D-Y"-D-Y"-E)$_r$—

-P-X-C$_n$-E-X'—C$_n$—Y-E-C$_n$—Y'-

-(P-X-C$_n$-E-X'—C$_n$—Y-E-C$_n$—Y'-)$_r$-.

The inventive method can include pretreatment or simultaneous treatment, or both, of the affected tissue with a suitable antibiotic. A suitable antibiotic is one that retains its potency when placed in physiological conditions. Some antibiotics are preferred for topical use on tissue, such as, but not limited to ciprofloxacin. The antibiotic can be included in the treatment using the microgel with or without the multifunctional hydrolase.

EXAMPLES

The example below is illustrative but does not limit the invention. The invention will now be described further in detail with respect to specific preferred embodiments by way of examples, it being understood that these are intended to be illustrative only and the invention is not limited to the materials, conditions, elements or process parameters, etc. recited therein.

Example 1

This example sets forth methods for preparing hydrogel and microgel used in the context of the invention.

The chemicals and materials used therefor were: Glycerol (Merck, Darrnstadt, GERMANY), Carbopol® polyanionic polymers (BFGoodrich Company, Specialty Polymers and Chemicals, Brecksville, Ohio), diisopropanol amine (Aldrich), distilled water, and 10% sodium hydroxide. The final concentrations of the component chemicals were: 23.5% w/v Glycerol stock (which is 87% w/w); 0.8% w/v of the desired polyanionic polymer; and distilled water and the sodium hydroxide (10%) or diisopropanol amine used to adjust the pH to 7.4 and make to volume.

Using standard sterile procedures, the carbopol was mixed in small amounts with distilled water under slow agitation with a propeller stirrer. The stirring continued until the powder was dissolved. Any trapped air was removed by reducing the pressure (water operated vacuum gauge). Glycerol was added under slow stirring and the pH was measured, and the 10% NaOH solution or the diisopropanol amine was used to adjust the composition to pH 7.4. Gelation occurred, resulting in a clear, transparent microgel. The resultant microgel was stored at 4° C.

Using the same methodology, but with weight to weight measurements of amounts, the following 10 g batches were made:

| Batch 1 | |
|---|---|
| Xanthan gum* | 0.6 g |
| Glycerol | 2.058 g |
| sodium hydroxide pellets | quantity sufficient |
| sterile water | quantity sufficient |
| Batch 2 | |
| Carbopol 934P | 0.08 g |
| Glycerol | 2.058 g |
| sodium hydroxide (10% w/w) | quantity sufficient |
| sterile water | quantity sufficient |
| Batch 3 | |
| Carbopol 934P | 0.04 g |
| Glycerol | 2.058 g |
| 40% w/w diisopropanolamine | quantity sufficient |
| sterile water | quantity sufficient |
| Batch 4 | |
| Carbopol 971P | 0.25 g |
| Glycerol | 2.058 g |
| 40% w/w diisopropanolamine | quantity sufficient |
| sterile water | quantity sufficient |
| Batch 5 | |
| Carbopol 974P | 0.08 g |
| glycerol | 2.058 g |
| 40% w/w diisopropanolamine | quantity sufficient |
| sterile water | quantity sufficient |

*Keltrol-T brand, supplied by Monsanto,

Example 2

Reaction Scheme for the Preparation of Compounds (5), (6), (7) and (8)

Preparation of 2-aminoethyl Acrylate Hydrochloride (5)

The amino group of 2-aminoethanol (Fluka) is protected with a tertbutyloxycarbonyl group (Boc) according to Bodanszky and Bodanszky [M. Bodanszky and A. Bodanszky, The practice of peptide synthesis, $2^{nd}$ edition, Springer Verlag, Berlin 1994]. Briefly, to a solution of 2-aminoethanol in 1 M NaOH and dioxane (1/1, v/v) is added 0.95 eq di-tert-butyl dicarbonate dropwise. After stirring for 1 h the dioxane is removed in vacuo, the aqueous solution is acidified with 1 M KHSO$_4$, and extracted with ethyl acetate. The organic layer is washed with brine, dried over Na$_2$SO$_4$, and concentrated in vacuo, obtaining the Boc-protected 2-aminoethanol.

To a solution of Boc-2-aminoethanol in DCM, 2 equivalents ("eq") triethylamine (TEA, Fluka) and 1.1 eq acryloylchloride (Aldrich) are added. After stirring for 3–4 h in the dark, the triethylaamine hydrochloride salt is removed by filtration over neutral alumina, and the filtrate concentrated in vacuo. The crude product is redissolved in ethyl acetate. The organic layer is washed with water, 1 M KHSO$_4$, 5% NaHCO$_3$, brine, dried over NaSO$_4$, and concentrated in vacuo yielding Boc-2-aminoethyl acrylate.

The Boc group is removed by adding a saturated solution of HCl in ether to a stirred solution of Boc-2-aminoethyl acrylate in DCM. After stirring for 1–2 h the reaction mixture is concentrated in vacuo obtaining 2-aminoethyl acrylate hydrochloride.

Preparation of (6), (7), and (8)

2-Hydroxyethyl acrylate (compound (4), Polysiences) and 2-aminoethyl acrylate (compound (5), preparation see above) can be dimerized by reaction with (tri)phosgene, or 1,1'-carbonyldiimidazole (CDI).

Preparation of (6) with Phosgene

To a solution of phosgene (1.1 eq) in toluene (Fluka, 20% phosgene in toluene), a mixture of compound (4) (1 eq) and diethylpropylamine ("DiPEA") (1.2 eq) in dichloromethane ("DCM") is added slowly over a period of 30 min. After stirring for an additional 10 min, a solution of compound (4) (1 eq) and DiPEA (1.2 eq) in DCM is added in one portion. The reaction mixture is stirred overnight, concentrated in vacuo and the residue redissolved in ethyl acetate. The organic layer is washed with 1 M KHSO$_4$, 5% NaHCO$_3$, brine, dried over NaSO$_4$, and concentrated in vacuo. The product is purified using column chromatography.

Preparation of (7) with CDI

To a solution of CDI (1.1 eq) in DCM, a mixture of compound (4) (1 eq) and DiPEA (1.2 eq) in DCM is added slowly over a period of 30 min. After stirring for an additional 10 min, a solution of compound (5) (1 eq) and DiPEA (2.2 eq) in DCM is added in one portion. The reaction mixture is stirred for 60 h, concentrated in vacuo and the residue redissolved in ethyl acetate. The organic layer is washed with 1 M KHSO$_4$, 5% NaHCO$_3$, brine, dried over NaSO$_4$, and concentrated in vacuo. The product is purified using column chromatography.

Preparation of (8) with Triphosgene

To a solution of triphosgene (0.37 eq) in DCM, a mixture of compound (5) (1 eq) and DiPEA (2.2 eq) in DCM is added slowly over a period of 30 min. After stirring for an additional 10 min, a solution of compound (5) (1 eq) and DIPEA (2.2 eq) in DCM is added in one portion. The reaction mixture is stirred overnight, concentrated in vacuo and the residue redissolved in ethyl acetate. The organic layer is washed with 1 M KHSO$_4$, 5% NaHCO$_3$, brine, dried over NaSO$_4$, and concentrated in vacuo. The product is purified using column chromatography.

Example 3

Reaction Scheme for the Preparation of Compounds (21), (24), (25), (26), and (27)

Preparation of Compound (21)

PEG (1 eq OH) was dissolved in toluene and dried by azeotropic distillation for 1 h using a Dean Stark water separator. After the reaction mixture was allowed to cool to 50° C., 4 eq acryloyl chloride and 4.4 eq TEA were added. After stirring 4 h-overnight in the dark, the triethylamine hydrochloride salt was removed by filtration over neutral alumina. After addition of 20 eq sodium carbonate to the filtrate, the mixture was stirred for 2 h and then filtrated over Hyflo® filtering aid. The filtrate was concentrated in vacuo, and the residue redissolved in a minimum amount of DCM. The product was obtained by precipitation of the DCM solution in stirred ice cold ether and dried in vacuo.

Preparation of Compounds (24) and (26)

PEG (1 eq OH) was dissolved in toluene and dried by azeotropic distillation for 1 h using a Dean Stark water separator. After the reaction mixture was allowed to cool to 50° C., L-lactide (1 eq) to obtain compound (24), n eq to obtain compound (26)) was added. The mixture was dried by azeotropic distillation for 1 h, and allowed to cool. When the temperature of the reaction mixture was about 50° C. 1 eq CaH$_2$ was added, and the reaction mixture was refluxed overnight. The reaction mixture was filtrated, concentrated in vacuo, and the residue redissolved in a minimum amount of DCM. The product was obtained by precipitation of the DCM solution in stirred ice cold ether, and dried in vacuo (80–100% yield).

Preparation of Compounds (25) and (27)

Compounds (24) and (26) were acrylated according to the procedure described above for the preparation of compound (21). Yields were 70–80%.

Example 4

Reaction Scheme for the Preparation of Compound (30)

Compound (30) was prepared by coupling PEG diacrylate via Michael-type addition to a thiol-functionalized PAA.

Preparation of S-Trityl-cysteamine

The thiol group of cysteamine hydrochloride (Fluka) was protected with a triphenyl methyl (trityl) group essentially according to Bodanszky and Bodanszky. In brief, 1 eq cysteamine hydrochloride was dissolved in DMF under heating (to 60° C.). After cooling the solution to 40° C., 1.1 eq triphenylmethanol (Fluka) was added. The reaction mixture was stirred at 60° C. for 30 min, and then allowed to cool to room temperature. After addition of 1.1 eq boron trifluoride etherate, the reaction mixture was stirred at 80° C. After the reaction was complete according to TLC the solvent was removed in vacuo. The solid product was dispersed in 5% NaHCO$_3$ and extracted with ethyl acetate until no solid was present in the water layer. The organic layer was washed with brine, dried over Na$_2$SO$_4$, and concentrated in vacuo, yielding 87% crude product. The product was dissolved in water, slightly acidified with 1 M KHSO4, resulting in a precipitate which was recrystallized in EtOAc/MeOH obtaining white crystals in a 75% yield.

Preparation of S-Trityl-2-mercaptoethylacrylamide

To a solution of S-Trityl-cysteamnine in DCM, 2 eq N,N-diisopropylethylamine (DiPEA, Fluka) and 1.1 eq acryloylchloride (Aldrich) were added. After stirring for 3–4 h in the dark, the reaction mixture was concentrated in vacuo, and the crude product was dissolved in ethyl acetate. The organic layer was washed with water, 1 M KHSO$_4$, 5% NaHCO$_3$, brine, dried over NaSO$_4$, arid concentrated in vacuo yielding S-trityl-2-mercaptoethylacrylamide in a quantitative yield.

Preparation of Thiol-derivatized PAA

Thiol-derivatized PAA was obtained by radical copolymerization of acrylic acid (AA, 19 eq) and S-trityl-2-mercaptoethylacrylamide (1 eq) in toluene using 2,2'-azobisisobutyronitrile ("AIBN") as initiator (monomer/initiator 100/1, mol/mol) in the presence of 19 eq TEA. After stirring overnight at 60° C., the reaction mixture was concentrated in vacuo. The product was purified by dialysis against aqueous NaOH, and water. After lyophilization P(AA-co-S-trityl-2-mercaptoethylacrylamide) was obtained.

The trityl group is removed by adding TFA to an aqueous solution of P(AA-co-S-trityl-2-mercaptoethylacrylamide) and triisopropylsilane (10 eq with regard to trityl groups) until pH 1. The polymer is purified by dialysis against dilute HOAc and water, and obtained by lyophilization.

Preparation of Compound (30)

Compound (30) is prepared by coupling of an acrylated PEG (e.g. compound 21, 25, or 27) via Michael-type addition to a thiol-functionalized PAA, e.g. in PBS (pH 8) 1 eq thiol groups are reacted with 1 eq acrylate groups.

Example 5

Reaction Scheme for the Preparation of Compound (35)

PAA crosslinked via ethylene glycol linkers can be obtained by radical copolymerization of AA and ethylene glycol diacrylate (Polysciences), e.g. in the ratio 500/1 (mol/mol). This copolymerization can be performed in an organic solvent (toluene) using AIBN as initiator. The polymer is purified by precipitation in icecold ether and dried in vacuo.

The copolymerization can also be done in an aqueous medium using 4,4'-azobis(4-cyanopentanoic acid) as initiator, after which the polymer is purified by dialysis against water.

Example 6

Reaction Scheme for the Preparation of Compound (40)

Preparation of Compound (38)

Ethylene glycol (1 eq OH) is dissolved in toluene and dried by azeotropic distillation for 1 h using a Dean Stark water separator. After the reaction mixture is allowed to cool to 50° C., L-lactide (1 eq) is added. The mixture is dried by azeotropic distillation for 1 h, and allowed to cool. When the temperature of the reaction mixture is about 50° C. 1 eq $CaH_2$ is added, and the reaction mixture is refluxed overnight. The reaction mixture is filtrated, and concentrated in vacuo, yielding compound (38).

Preparation of Compound (40)

To a solution of compound (38) (1 eq) and PAA (500 eq COOH) in DCM is added 1 eq diisopropylcarbodiimide and 1 eq dimethylaminopyridine. The reaction mixture is stirred overnight. The solvents are removed in vacuo and the crude product is redissolved in a minimum amount of DCM. The product is isolated by precipitation in ice-cold diethyl ether and dried in vacuo.

Example 7

Reaction Scheme for the Preparation of Compound (43)

Preparation of (43) with Phosgene

To a solution of phosgene (1.1 eq) in toluene (Fluka, 20% phosgene in toluene), a mixture of compound (41) (1 eq OH) and DiPEA (1.2 eq) in DCM is added slowly over a period of 30 min. After stirring for an additional 10 min, a solution of PEG (1 eq OH) and DIPEA (1.2 eq) in $DC^M$ is added in one portion. The reaction mixture is stirred overnight, concentrated in vacua and the residue redissolved in a minimum amount of DCM. The product is isolated by precipitation in ice-cold diethyl ether and dried in vacuo.

Example 8

Reaction Scheme for the Preparation of Compounds (44), (45), and (46)

Preparation of Compound (44)

Compound (41) (1 eq OH) is dissolved in toluene and dried by azeotropic distillation for 1 h using a Dean Stark water separator. After the reaction mixture is allowed to cool to 50° C., 1 eq L-lactide was added. The mixture is dried by azeotropic distillation for 1 h, and allowed to cool. When the temperature of the reaction mixture is about 50° C. 1 eq CaH2 was added, and the reaction mixture is refluxed overnight. The reaction mixture is filtrated, concentrated in vacuo, and the residue redissolved in a minimum amount of DCM. The product is obtained by precipitation of the DCM solution in stirred ice cold ether, and dried in vacua.

Preparation of Compound (45) with Phosgene

To a solution of phosgene (1.1 eq) in toluene (Fluka, 20% phosgene in toluene), a mixture of compound (44) (1 eq OH) and DiPEA (1.2 eq) in DCM is added slowly over a period of 30 min. After stirring for an additional 10 min, a solution of compound (44) (1 eq OH) and DiPEA (1.2 eq) in DCM is added in one portion. The reaction mixture is stirred overnight, concentrated in vacuo and the residue redissolved in a minimum amount of DCM. The product is isolated by precipitation in ice-cold diethyl ether and dried in vacuo.

Preparation of Compound (46) with CDI

To a solution of CDI (1.1 eq) in DCM, a mixture of compound (41) (1 eq OH) and DiPEA (1.2 eq) in DCM is added slowly over a period of 30 min. After stirring for an additional 10 min, a solution of compound (44) (1 eq OH) and. DiPEA (1.2 eq) in DCM is added in one portion. The reaction mixture is stirred for 60 h, concentrated in vacuo and the residue redissolved in a minimum amount of DCM. The product is isolated by precipitation in ice-cold diethyl ether and dried in vacuo.

The foregoing examples serve to demonstrate the practice and usefulness of the invention and in no way should they be construed as limiting the scope of the invention.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A composition comprising a pre-formed, hydrolytically susceptible non-addition polyanionic polymer comprising polymer strands formed from at least one ethylenically unsaturated monomer, wherein the polymer strands are linked by at least one linking moiety comprising a hydrolytically susceptible bond formed with a multidentate compound comprising two or more ethylenically unsaturated moieties, each such moiety being linked to the multidentate compound through a hydrolytically susceptible bond, wherein at least one of which monomers has:
   i) one or more functional groups that can be titrated with base to form negatively charged functional groups, or
   ii). one or more precursor groups that are precursors of the functional groups that can be titrated with base; which precursor groups are converted to the functional groups;
   wherein at least one of the ethylenically unsaturated monomers is according to the formula:

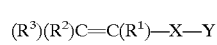

$(R^3)(R^2)C=C(R^1)-X-Y$ wherein:
   Y is $-C(O)OR^4$; $-O-S(O_2)OR^4$; $-S(O_2)OR^4$; or $-S(O)OR^4$; wherein $R^4$ is hydrogen or a cleavage permitting group;
   X is a direct bond; a straight or branched alkylene group having one to six carbon atoms, one or more of which can be replaced by O, S, or N heteroatoms, provided that there is no heteroatom in a position α or β to Y; phenylene; a five or six membered heteroarylene having up to three heteroatoms independently selected from O, S, and N, provided that neither Y or $(R^3)(R^2)C=C(R^1)-$ is bonded to a heteroatom; and
   $R^1$, $R^2$ and $R^3$ are independently selected from, hydrogen, $C_1-C_6$ alkyl, carboxy, halogen, cyano, isocyanato, $C_1$–$C_6$ hydroxyalkyl, alkoxyalkyl having 2 to 12 carbon atoms, $C_1$–$C_6$ haloalkyl, $C_1$–$C_6$ cyanoalkyl, $C_3$–$C_6$ cycloalcyl, $C_1$–$C_6$ carboxyalkyl, aryl, hydroxyaryl, haloaryl, cyanoaryl, $C_1$–$C_6$ alkoxyaryl, carboxyaryl, nitroaryl, or a group —X—Y; wherein $C_1$–$C_6$ alkyl or $C_1$–$C_6$ alkoxy groups are either linear or branched and up to Q-2 carbon atoms of any $C_3$–$C_6$ cycloalkyl group, wherein Q is the total number of ring carbon atoms in the cycloalkyl group, are independently replaced with O, S, or N heteroatoms; with the proviso that neither doubly-bonded carbon atom is directly bonded to O or S; and wherein aryl is phenyl or a 5 or 6 membered heteroaryl having up to three heteroatoms selected from the group consisting of O, S, and N.

2. The composition of claim 1, wherein the linking moiety is formed by copolymerization of an ethylenically unsaturated linking agent, and the mole fraction of ethylenic double bonds in the combination from which the polyanionic polymer is made that is contributed by the ethylenically unsaturated linking agent is 0.02 or less.

3. The composition of claim 1, comprising a microgel formed of the polyanionic polymer.

4. The composition of claim 3, wherein the microgel has a ratio of the macroviscosity of the microgel to the microviscosity of the microgel is 10,000 or less.

5. The composition of claim 1, wherein the polyanionic polymer is functionalized to provide one or more pendant functional groups selected from hydroxy, acyl halide, chloroformate, and mercapto; and wherein the linking moiety provides crosslinking and is a reaction product of the pendant groups between polymer segments or between the pendant groups and complementing functions groups of a linking group.

6. The composition of claim 5, wherein the linking agent is the diacrylate of an α,ω-diol or the diacrylate of a chain extended α,ω-diol.

\* \* \* \* \*